United States Patent [19]

Lautenschlager et al.

[11] 4,203,223
[45] May 20, 1980

[54] PERIODONTAL PROBE

[75] Inventors: Eugene P. Lautenschlager, Skokie; Peter J. Robinson, Kenilworth; Randall M. Vitek, Brookfield, all of Ill.

[73] Assignee: Northwestern University, Evanston, Ill.

[21] Appl. No.: 3,130

[22] Filed: Jan. 12, 1979

[51] Int. Cl.² .............................................. A61C 3/00
[52] U.S. Cl. ....................................... 433/75; 433/141
[58] Field of Search ......................... 128/776; 32/40 R

[56] References Cited

U.S. PATENT DOCUMENTS

| 3,058,225 | 10/1962 | Ward | 128/776 |
| 3,935,640 | 2/1976 | Cohan | 32/40 R |
| 3,943,914 | 3/1976 | Grenfell | 32/40 R |

OTHER PUBLICATIONS

Hassell et al., Periodontal Probing: Interinvestigator Discrepancies and Correlations between Probing Force and Recorded Depth, Helv. Odont. Acta 17:38-42 (Apr. 1973).
Listgarten et al., Periodontal Probing and the Relationship of the Probe Tip to Periodontal Tissues, J. Periodontal, 511-513, (Sep. 1976).
Armitage et al., Microscopic Evaluation of Clinical Measurements of Connective Tissue Attachment Levels, J. Clin. Periodontology, 4:173-190 (1977).
Glickman, Clinical Periodontology, 549-551, (4th Ed., W. B. Saunders & Co., 1972).
Gabathuler et al., A Pressure-Sensitive Periodontal Probe, Helv. Odont. Acta 15:114-117 (Oct. 1971).

Primary Examiner—Robert Peshock
Attorney, Agent, or Firm—Tilton, Fallon, Lungmus & Chestnut

[57] ABSTRACT

A force-controlled periodontal probe is disclosed, the probe having a scale-marked shaft slidably carried by an alignment sleeve at the head end of the instrument and urged into a normally extended condition by a thin leaf spring. Measurements of gingival sulcus depths are taken when the force applied by the periodontist to the handle of the instrument and the resistance to further penetration by the tip portion of the shaft have caused the shaft to shift into an indicated displaced position. In that position the spring exerts a predetermined and accurately reproducible probing force.

13 Claims, 4 Drawing Figures

U.S. Patent  May 20, 1980  4,203,223
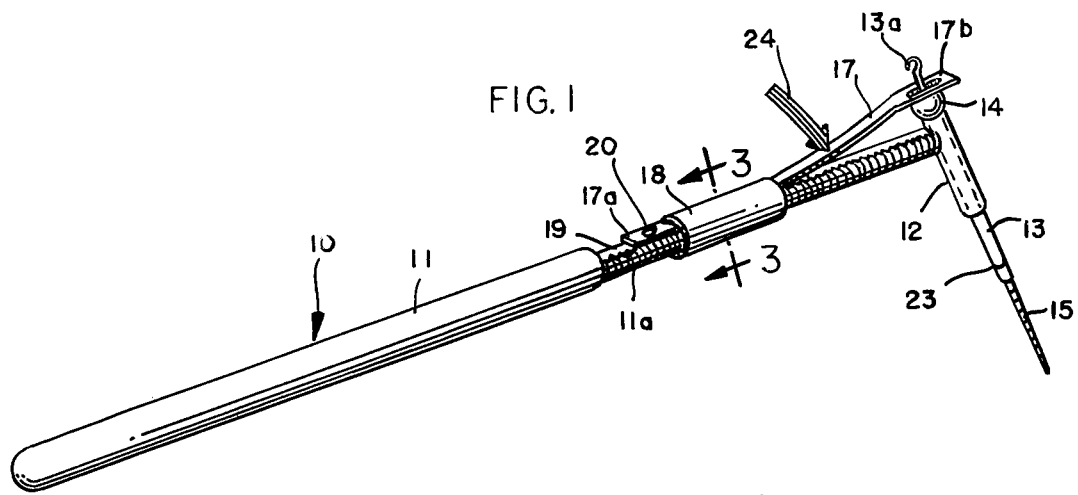
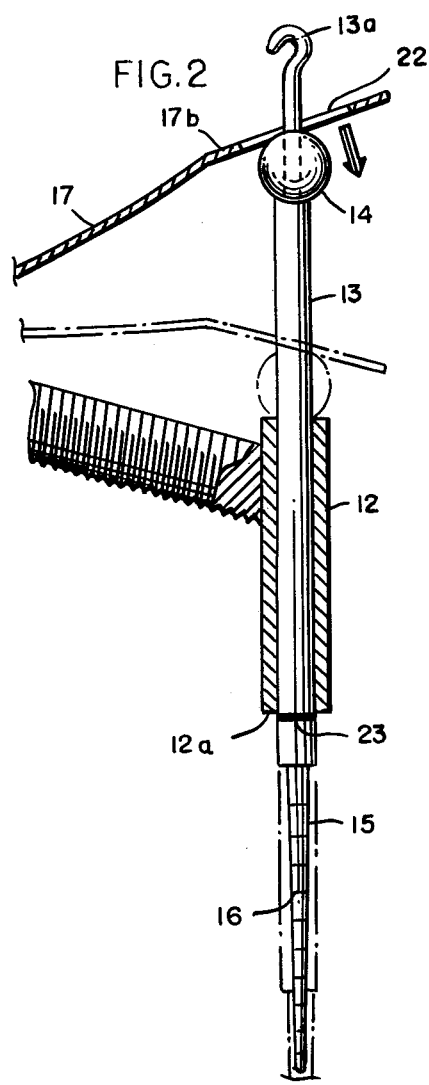
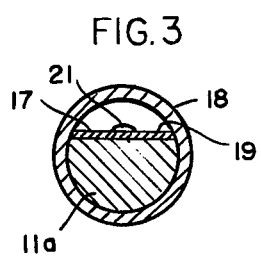
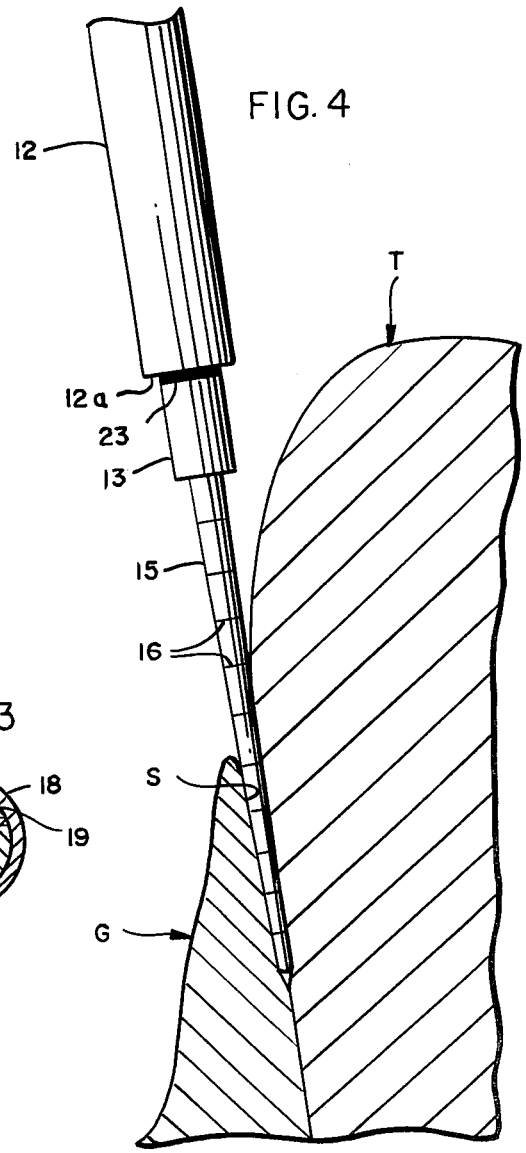

PERIODONTAL PROBE

BACKGROUND AND SUMMARY

Periodontal sulcus probing is a standard clinical technique for ascertaining periodontal and gingival condition. In such a procedure, the periodontist applies light hand pressure to the handle of the instrument to insert a thin rod-like probe tip into the sulci between the teeth and gingiva. Scale markings on the tip give a visual indication of the extent of penetration and, in particular, reveal the depth of periodontal pockets (diseased sulci) that may exist. The technique is described fully in publications such as Listgarten et al, Periodontal Probing and the Relationship of the Probe Tip to Periodontal Tissues, J. Periodontal. 511-413 (September 1976; Armitage et al, Microscopic Evaluation of Clinical Measurements of Connective Tissue Attachment Levels, J. Clin. Periodontology, 4:173-190 (1977); Hassell et al, Periodontal Probing: Interinvestigator Discrepancies and Correlations between Probing Force and Recorded Depth, Helv. Odont. Acta 17:38-42 (April 1973); Gabathuler et al, A Pressure-Sensitive Periodontal Probe, Helv. Odont. Acta 15:114-117 (October 1971); Glickman, Clinical Periodontology, 549-551 (4th Ed., W.B. Saunders & Co., 1972).

Pressure-sensitive periodontal probes have been used experimentally in an effort to ascertain the forces commonly applied by clinicians during such probing, and to investigate discrepancies and correlations between probing force and recorded depth. Thus, in Hassell et al, Supra, forces and depths were measured by using a probe equipped with a piezoelectric sensor and a charge amplifier, and in Armitage et al, Supra, releasable plastic probe tips were deposited and cemented in the sulci or pockets of dogs, using a probe for applying consistent insertion forces, after which the dogs were sacrificed and the placement of the tips were histologically studied. Such investigations indicate that there are significant differences in probing force and detected depth for different clinicians. Even the same clinician may apply different probing force at different times or circumstances. Consistent depth readings require a readily ascertainable uniform force, but heretofore there has been no simple and reliable clinical device for assisting periodontists in establishing and controlling the forces applied by the tips of the instruments during periodontal probing procedures.

A main object of this invention therefore lies in providing a simple and easily used periodontal probe which can consistently measure gingival pocket depths utilizing the same applied force at each and every site. Another object is to provide a probe which can be readily manipulated to apply a constant predetermined probing force but which, at the same time, is durable, easily cleaned and sterilized, and sufficiently free of mechanical and/or electrical complexity and bulk to facilitate use by a periodontist following the same procedures used with conventional probes. A still further object is to provide a periodontal probe which is constructed so that the force applied by the tip of the probe may be temporarily selectively increased by the periodontist during those moments when so depth reading is to be taken, for example, when the tip of the probe is being directed towards a sulcus and detached soft tissue must be displaced before measurements of pocket depth can begin.

In brief, the probe includes a handle provided at its head end with a transversely-extending sleeve, the sleeve slidably receiving a probe shaft. A thin leaf spring is secured at one end to the handle and engages bearing means provided by the probe shaft to urge that shaft in one direction. During a probing procedure, the leaf spring permits displacement of the shaft when the tip of that shaft is inserted into a gingival pocket. A depth reading is made from scale or fiducial markings on the probe tip while the tip is being pushed just hard enough to displace the shaft a predetermined extent against the force exerted by the leaf spring. Such extent of displacement is visually determined and is representative of a predetermined probing force to be applied by the instrument at the time a depth reading is to be taken. Because the leaf spring extends generally along the handle of the instrument near the head end thereof, a user may, if desired, increase the force to be applied by the probe tip simply by placing his index finger upon that spring as the probe tip is advanced.

Other advantages, objects, and features of the invention will become apparent from the specification and drawings.

DRAWINGS

FIG. 1 is a perspective view of a periodontal probe embodying the present invention.

FIG. 2 is an enlarged fragmentary sectional view showing the head end of the instrument with the probe shaft in its displaced or retracted position.

FIG. 3 is a greatly enlarged cross sectional view taken along line 3—3 of FIG. 1.

FIG. 4 is an enlarged elevational view showing the use of the probe in measuring pocket depth.

DETAILED DESCRIPTION OF PREFERRED EMBODIMENT

Referring to FIG. 1, the numeral 10 generally designates a periodontal probe having an elongated handle 11 having a generally transversely extending sleeve 12 at the head end thereof. The tubular sleeve slidably receives a probe shaft 13. The shaft is provided with a rounded or spherical thrust bearing 14 adjacent one end (the upper end of the shaft when the instrument is oriented as shown in FIG. 1) and is provided at its opposite end with an elongated tip portion 15. Scale markings 16 (FIG. 4) are provided along the tip portion of the probe shaft; in accordance with the practice adopted for conventional periodontal probes, such markings may be one millimeter apart and extend along approximately one centimeter of the length of the tip.

As indicated in FIG. 3, the bearing element 14 is of substantially larger diameter than the main body of the shaft 13 and may be secured to a pin extension 13a of that shaft. Alternatively, the bearing element may be formed integrally with the remainder of the shaft. In either event, pin 13a projects beyond the bearing element (FIGS. 1 and 2) and, because the bearing element is larger than the internal diameter of sleeve 12, that element serves as a stop to limit downward movement of the shaft, that is, movement in a direction that results in extension of probe tip 15.

A thin elongated leaf spring 17 extends in the general direction of handle 11 adjacent the head end thereof. One end 17a of the spring is secured to the handle by means of a collar 18 carried by the threaded neck portion 11a of the handle. As shown most clearly in FIG. 3, the neck portion of the handle is recessed along one side to provide a flattened surface 19 to support end portion 17a of the spring. The end portion 17a of the spring may be welded or otherwise permanently secured to the handle or, as in the illustration given, the spring may be provided with a small opening 20 which receives an enlargement or projection 21 from the flat surface 19 of the handle for the purpose of locking the spring and handle against independent longitudinal movement.

The opposite end 17b of the leaf spring is provided with a longitudinally elongated opening or slot 22 which receives the pin 13a of shaft 13. In an untensioned state, leaf spring 17 is generally planar (except for end portion 17b which may have an angular offset as shown) so that when the instrument is in the normal non-operating condition shown in FIG. 1 the tension of spring 17 urges probe shaft 13 into the extended position shown with thrust bearing 14 engaging one end of sleeve 12 and thereby serving both as a bearing element and as a stop element.

It will be observed that the shaft is provided with a suitable indicia mark 23 which may, if desired, be scribed to insure permanency, and which acts together with the adjacent end 12a of the sleeve to provide a visual indication of the extent of displacement which the shaft must undergo to flex spring 17 so that a precise predetermined force will be applied by the tip 15 of the probe.

Such applied force should have a selected value within the range of about 10 to 80 ponds, the preferred range being about 20 to 30 ponds (1 pond equals 1 gram of force). For example, an instrument may be manufactured to exert a force of 25 ponds at its probe tip when that tip is urged against a surface to cause displacement of the shaft into the retracted position depicted in FIG. 2.

Over an extended period of use, or because of abusive treatment, it is possible that spring 17 might become weakened or distorted to exert a force slightly more or less than the desired force when the shaft is fully retracted. In such a case, correction may be made by threading collar 18 one way or the other along the neck 11a to alter the force exerted by the spring. Or if desired, a user may adjust collar 18 so that spring 17 exerts a predetermined force which is either greater or less than the original value. While such adjustability would be advantageous in many circumstances, it is to be understood that in a simplified version of the instrument the end 17a of the spring might simply be secured to the handle and the threads of neck 11a, as well as collar 18, might be eliminated.

Adjustment of spring tension, or verification of selected tension, for the probe depicted in the drawings is facilitated by the provision of a small hook at the end 13a of the shaft. The instrument is simply inverted so that shaft 13 extends vertically with the hook facing downwardly, and a weight of 25 grams or any other selected value is suspended from the hook. The user then simply observes whether the mark 23 comes to rest at the end of sleeve 12; if it does not, then collar 18 is rotated one way or the other to recalibrate the instrument.

FIG. 4 illustrates the instrument in use with the tip portion 15 of the probe inserted into the sulcus S between gingival tissue G and tooth T. The probe shaft is displaced to bring marking 23 to the end 12a of sleeve 12. The preselected probing force at which depth measurements are to be taken is therefore being applied by the probe tip. The clinician simply observes the instrument to make certain that the displacement marking 23 is aligned with end surface 12a, and then takes a pocket depth reading by observing the scale markings 16 which remain exposed above the gingival line.

It is essential that the instrument be constructed so that adequate but not excessive movement of the probe shaft occurs as that shaft is shifted between the two positions depicted in FIG. 2. If the extent of movement is insufficient, a periodontist may find it virtually impossible to observe whether the displacement required for pocket depth measurement has occurred. Even if such movement were detected, a slight error in visually aligning mark 23 of the shaft with the end 12a of the sleeve might result in a substantial difference in the applied force. On the other hand, if the instrument were constructed so that the extent of displacement were excessive, then manipulation of the instrument in a patient's mouth might be difficult or even impossible. To be adequate without being excessive, the displacement should therefore fall within the general range of about ½ to 2 centimeters, with a displacement of about 1 centimeter being found particularly effective. In view of the size constraints for the instrument as a whole, and the further requirements for reliability, durability, and structural simplicity, it is believed that the desired extent of shaft displacement, and the application of an accurate and reproducible force when the shaft is so displaced, require the use of a leaf spring as disclosed herein, in contrast to a coiled tension or compression spring.

The thin leaf spring not only provides a highly effective means for applying the gentle force necessary for taking depth measurements but also provides a high degree of flexibility in the use of the instrument to the extent that the user may selectively increase and even override the force of the spring by simply placing his index finger (of the same hand that holds the instrument) upon the spring as generally indicated by arrow 24 in FIG. 1. For example, in some instances a periodontist may wish to increase the force exerted by the spring in order to facilitate initial insertion of the probe tip into the sulcus. In such a case, gentle finger pressure at 24 would tend to contribute to the ease of entry while at the same time increasing tactile sensitivity to the extent that resistance encountered by the probe may be directly sensed by the finger in engagement with the spring. Once entry is accomplished and a depth reading is to be taken, the clinician simply removes his finger from the spring and advances the probe until it is fully displaced or retracted (FIGS. 2 and 4).

While in the foregoing we have disclosed an embodiment in considerable detail for purposes of illustration, it will be understood by those skilled in the art that many of these details may be varied without departing from the spirit and scope of the invention.

We claim:

1. A periodontal probe comprising an elongated handle having a head end provided with a generally transversely-extending sleeve; a probe shaft slidably supported by said sleeve, said shaft including an elongated tip at one end thereof and bearing means at the opposite end thereof; a leaf spring having one end secured to said handle and an opposite end engaging said bearing means for urging said shaft in one direction to extend said tip away from said sleeve, the force exerted by said spring upon said shaft progressively increasing as said shaft is displaced in a direction opposite from said one direction; stop means for limiting the extent of movement of said shaft in said one direction; and means provided by said shaft and sleeve for indicating when said shaft is retracted to a point at which said spring exerts an extending force of predetermined magnitude upon said shaft.

2. The probe of claim 1 in which said probe tip is provided with spaced scale markings for indicating the depth of insertion of said tip in a gingival sulcus at said force of predetermined magnitude.

3. The probe of claim 1 in which means are provided for adjusting the force exerted by said spring upon said bearing means.

4. The probe of claim 3 in which said means for adjusting said force includes a collar threadedly mounted upon said handle near said head end thereof, said one end of said leaf spring extending through said collar, whereby, screwing said collar one way or the other along said handle varied the length of the spring between said collar and bearing means and thereby alters the force exerted by said spring upon said bearing means.

5. The probe of claim 1 in which said bearing means comprises an enlargement of said shaft adjacent said opposite end thereof, said enlargement providing a rounded bearing surface engaging said spring.

6. The probe of claim 5 in which said enlargement has a diameter greater than the inside diameter of said sleeve and also serves as said stop means for limiting the extent of movement of said shaft in said one direction.

7. The probe of claim 6 in which said enlargement comprises a generally spherical element secured to said shaft adjacent said opposite end thereof.

8. The probe of claim 6 in which said spring is provided with a slot adjacent said opposite end thereof, said shaft being provided with a pin extending through said slot for operatively connecting said probe shaft and spring together.

9. The probe of claim 1 in which said means provided by said shaft and sleeve for indicating when said shaft is displaced to a point at which said spring exerts said force of predetermined magnitude comprises an indicia mark on said shaft alignable with an end portion of said sleeve when said shaft is so displaced.

10. The probe of claims 1, 3, 5, or 9 in which said leaf spring has a substantial portion of its length extending in normally spaced relation along a side of said handle opposite from said probe shaft tip, whereby, finger pressure may be applied to said spring to increase the resistance against shaft displacement.

11. The probe of claims 1, 3, or 9 in which the extent of movement of said shaft between the point at which said stop means limits the movement of said shaft in said one direction and the point at which said means indicates that a force of predetermined magnitude is exerted falls within the range of about $\frac{1}{2}$ to 2 centimeters.

12. The probe of claims 1, 3, or 9 in which the extent of movement of said shaft between the point at which said stop means limits the movement of said shaft in said one direction and the point at which said means indicates that a force of predetermined magnitude is exerted is about 1 centimeter.

13. The probe of claim 1 in which said shaft is provided with a hook adjacent said opposite end thereof for suspending a calibrating weight therefrom.

* * * * *